(12) United States Patent
Irisawa et al.

(10) Patent No.: US 10,342,435 B2
(45) Date of Patent: Jul. 9, 2019

(54) PHOTOACOUSTIC MEASUREMENT APPARATUS AND PROBE FOR PHOTOACOUSTIC MEASUREMENT APPARATUS

(71) Applicant: FUJIFILM Corporation, Tokyo (JP)

(72) Inventors: Kaku Irisawa, Ashigarakami-gun (JP); Takeya Abe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 732 days.

(21) Appl. No.: 14/643,346

(22) Filed: Mar. 10, 2015

(65) Prior Publication Data
US 2015/0173626 A1 Jun. 25, 2015

Related U.S. Application Data

(63) Continuation of application No. PCT/JP2013/073413, filed on Aug. 30, 2013.

(30) Foreign Application Priority Data

Sep. 28, 2012 (JP) .................................. 2012-216126

(51) Int. Cl.
*A61B 5/00* (2006.01)
*A61B 8/00* (2006.01)
(Continued)

(52) U.S. Cl.
CPC .............. *A61B 5/0095* (2013.01); *A61B 8/12* (2013.01); *A61B 8/445* (2013.01);
(Continued)

(58) Field of Classification Search
CPC .................... A61B 5/0095; G01N 29/2418
See application file for complete search history.

(56) References Cited

U.S. PATENT DOCUMENTS 4,718,417 A * 1/1988 Kittrell ............... A61B 1/00183
600/317
6,387,044 B1 * 5/2002 Tachibana .......... A61B 1/00135
600/114

(Continued)

FOREIGN PATENT DOCUMENTS

CN 201954462 U 8/2011
JP 57-31834 A 2/1982
(Continued)

OTHER PUBLICATIONS

Chinese Office Action, dated Feb. 3, 2016, for Chinese Application No. 201380047038.8 , along with an English machine translation.
(Continued)

*Primary Examiner* — Tse W Chen
*Assistant Examiner* — Jason M Ip
(74) *Attorney, Agent, or Firm* — Birch, Stewart, Kolasch & Birch, LLP

(57) ABSTRACT

The light irradiation range of a probe for a photoacoustic measurement apparatus is increased. The probe for a photoacoustic measurement apparatus includes a light transmission unit that irradiates a subject with light, and a photoacoustic wave detector 52 that detects a photoacoustic wave generated from the subject. The light transmission unit includes light propagation part 51 for propagating light, and a light transmission member 55. Further, the light transmission member 55 includes an inner peripheral surface 55*a* that is formed in the shape of a curved concave surface and an outer peripheral surface 55*b* that has a radius of curvature larger than the radius of curvature of the inner peripheral surface 55*a* and is formed in the shape of a curved convex surface. The outer peripheral surface 55*b* is disposed so that the light L emitted from the light propagation part 51 is incident on the inner peripheral surface 55*a*.

18 Claims, 20 Drawing Sheets

(51) Int. Cl.
*A61B 8/12* (2006.01)
*G01N 29/24* (2006.01)
*G01N 21/17* (2006.01)

(52) U.S. Cl.
CPC ..... *G01N 21/1702* (2013.01); *G01N 29/2418* (2013.01); *A61B 8/4427* (2013.01); *A61B 8/4483* (2013.01)

(56) References Cited

U.S. PATENT DOCUMENTS

| | | | |
|---|---|---|---|
| 2005/0004458 A1 | 1/2005 | Kanayama et al. | |
| 2005/0043627 A1* | 2/2005 | Angelsen | B06B 1/0292 600/459 |
| 2005/0117845 A1* | 6/2005 | Hirose | C03C 25/105 385/39 |
| 2008/0177138 A1* | 7/2008 | Courtney | A61B 5/0062 600/109 |
| 2010/0244812 A1 | 9/2010 | Sasaki | |
| 2010/0298688 A1* | 11/2010 | Dogra | A61B 5/0084 600/407 |

FOREIGN PATENT DOCUMENTS

| | | |
|---|---|---|
| JP | 2004-351023 A | 12/2004 |
| JP | 2005-21380 A | 1/2005 |
| JP | 2011-10827 A | 1/2011 |
| WO | WO 2009/069379 A1 | 6/2009 |

OTHER PUBLICATIONS

Japanese Notice of Reasons for Rejection and English translation thereof, dated Oct. 27, 2015, for Japanese Application No. 2012-216126.

International Search Report, issued in PCT/JP2013/073413, dated Nov. 26, 2013.

Wang et al., "A High-Speed Photoacoustic Tomography System based on a Commercial Ultrasound and a Custom Transducer Array", Proc. of SPIE, Feb. 23, 2010, vol. 7564, No. 756424, pp. 1-9.

Written Opinion of the International Searching Authority, issued in PCT/JP2013/073413, dated Nov. 26, 2013.

* cited by examiner

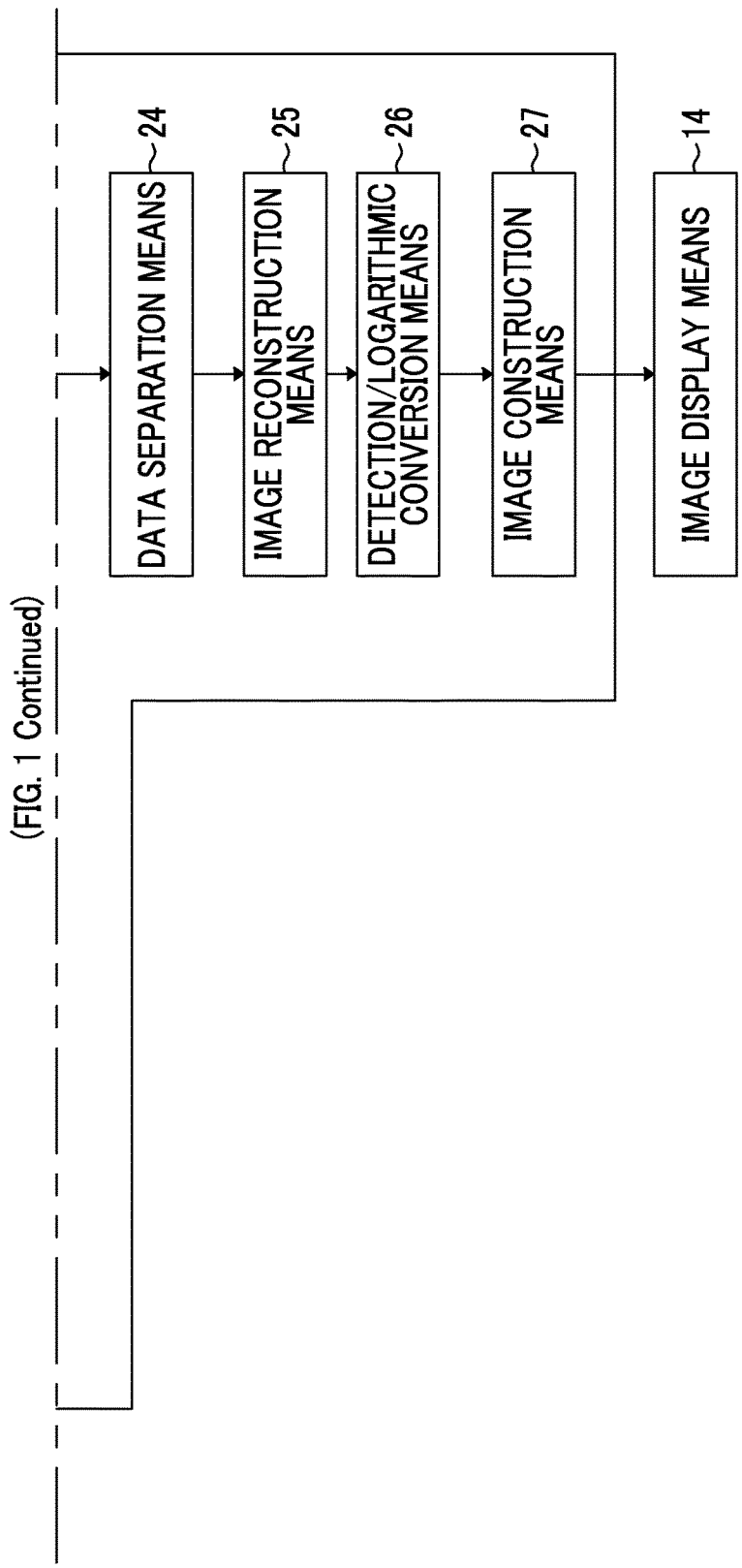

PHOTOACOUSTIC MEASUREMENT APPARATUS AND PROBE FOR PHOTOACOUSTIC MEASUREMENT APPARATUS

CROSS-REFERENCE TO RELATED APPLICATIONS

This application is a Continuation of PCT International Application No. PCT/JP2013/073413 filed on Aug. 30, 2013, which claims priority under 35 U.S.C. § 119(a) to Japanese Patent Application No. 2012-216126 filed on Sep. 28, 2012. Each of the above applications is hereby expressly incorporated by reference, in its entirety, into the present application.

BACKGROUND OF THE INVENTION

1. Field of the Invention

The present invention relates to a photoacoustic measurement apparatus, that is, an apparatus for irradiating a subject, such as biological tissue, with light and performing processing for imaging the subject on the basis of a photoacoustic wave generated with light irradiation, or the like.

Further, the invention relates to a probe that is used in this kind of photoacoustic measurement apparatus.

2. Description of the Related Art

For some time, a photoacoustic imaging apparatus, which images the inside of a living body by using a photo-acoustic effect, has been known, as disclosed in, for example, JP2005-21380A and A High-Speed Photoacoustic Tomography System based on a Commercial Ultrasound and a Custom Transducer Array, Xueding Wang, Jonathan Cannata, Derek DeBusschere, Changhong Hu, J. Brian Fowlkes, and Paul Carson, Proc. SPIE Vol. 7564, 756424 (Feb. 23, 2010). In the photoacoustic imaging apparatus, the inside of the living body is irradiated with pulsed light such as a pulsed laser beam. In the inside of the living body that has been irradiated with the pulsed light, the volume of biological tissue having absorbed the energy of the pulsed light is expanded by heat and the biological tissue generates a photoacoustic wave (acoustic signal). Accordingly, the photoacoustic wave is detected with an ultrasonic probe or the like, and the visible image of the inside of the living body can be formed on the basis of a detected signal.

In the other hand, an ultrasonic imaging apparatus using an ultrasonic probe also is well-known as disclosed in WO2009/069379A and JP2011-10827A. This kind of ultrasonic probe includes an ultrasonic transducer at an end thereof. In many cases, the ultrasonic probe includes a backing material, a piezoelectric body, electrodes between which the piezoelectric body is interposed, an acoustic matching layer, an acoustic lens, and the like. In the ultrasonic imaging apparatus, an ultrasonic wave is applied to a subject, such as the human body, from the ultrasonic transducer and an ultrasonic wave reflected from the subject is received by the ultrasonic transducer. Further, a detection signal of the reflected ultrasonic wave is electrically processed, so that an ultrasonic image is obtained.

Meanwhile, in this specification, an elastic wave generated from the probe is referred to as an ultrasonic wave and an elastic wave generated due to a photo-acoustic effect is referred to as a photoacoustic wave.

Since the above-mentioned ultrasonic probe can detect not only an ultrasonic wave but also a photoacoustic wave, the ultrasonic probe is also widely used in photoacoustic measurement apparatuses. That is, in this kind of apparatus, a light irradiating unit, which irradiates a subject with light, is added to the ultrasonic probe and a photoacoustic wave, which is generated from the subject receiving light from the light irradiating unit, is detected by an ultrasonic transducer of the ultrasonic probe.

SUMMARY OF THE INVENTION

Incidentally, when a portion of the subject is imaged in the photoacoustic imaging apparatus using the photo-acoustic effect of, it is preferable that a wider range of the subject be irradiated with light so that a wider area can be imaged at one time. Such a request applies not only to the photoacoustic imaging apparatus, but also to a photoacoustic measurement apparatus that performs various kinds of measurement other than imaging using a photo-acoustic effect.

The invention has been made in consideration of the above-mentioned circumstances, and an object of the invention is to provide a probe for a photoacoustic measurement apparatus that can irradiate a wide range of an object to be measured, with light, and a photoacoustic measurement apparatus.

A probe for a photoacoustic measurement apparatus according to the invention includes a light transmission unit that irradiates a subject with light, and a photoacoustic wave detector that detects a photoacoustic wave generated from a portion of the subject irradiated with light. The light transmission unit includes a light propagation part, such as an optical fiber, for propagating light emitted from a light source, and a light transmission member that includes an inner peripheral surface formed in the shape of a curved concave surface and an outer peripheral surface having a radius of curvature larger than the radius of curvature of the inner peripheral surface and formed in the shape of a curved convex surface and is disposed so that light emitted from the light propagation part is incident on the inner peripheral surface.

Meanwhile, it is particularly preferable that the inner and outer peripheral surfaces of the light transmission member be formed, in shapes having curvatures, in one common plane.

Further, in the probe for a photoacoustic measurement apparatus of the invention, it is preferable that the photoacoustic wave detector include a convex outer end face and the outer peripheral surface of the light transmission member be formed so as to be curved along the convex outer end face of the photoacoustic wave detector.

Furthermore, in the probe for a photoacoustic measurement apparatus of the invention, it is preferable that the probe further include a light guide member, which uniformizes the distribution of the intensity of light emitted from the light propagation part, be disposed between the inner peripheral surface of the light transmission member and the light propagation part.

Moreover, in the probe for a photoacoustic measurement apparatus of the invention, it is preferable that at least a part of the light guide member face at least a part of an end face of the light transmission member that connects the inner and outer peripheral surfaces of the light transmission member.

Further, it is preferable that the light guide member be formed in a tapered shape so that the cross-sectional area of the light guide member is gradually increased from the light propagation part toward the light transmission member.

Furthermore, in the probe for a photoacoustic measurement apparatus of the invention, it is preferable that the probe further include a light diffusion member be disposed between the light guide member and the light propagation part.

It is preferable that the light diffusion member of which the degree of light diffusion in one direction is lower than the degree of light diffusion in a direction orthogonal to the one direction be applied as the light diffusion member. Specifically, examples of this kind of the light diffusion member include a light diffusion member of which a light diffusion pattern has an elliptical shape.

Moreover, in the probe for a photoacoustic measurement apparatus of the invention, it is preferable that the probe further include a lens having negative power be disposed at a position that faces the inner peripheral surface of the light transmission member.

Meanwhile, when the above-mentioned light guide member is provided, the lens having negative power is disposed between the light guide member and the inner peripheral surface of the light transmission member.

On the other hand, a photoacoustic measurement apparatus according to the invention includes the above-mentioned probe for a photoacoustic measurement apparatus according to the invention.

According to the probe for a photoacoustic measurement apparatus of the invention, there is provided a light transmission member that includes an inner peripheral surface formed in the shape of a curved concave surface and an outer peripheral surface having a radius of curvature larger than the radius of curvature of the inner peripheral surface and formed in the shape of a curved convex surface and is disposed so that light emitted from the light propagation part is incident on the inner peripheral surface. Accordingly, the light, which is incident on the light transmission member from the light propagation part, is emitted from the light transmission member in an angular range that is larger than an emission angle obtained when light is emitted from the light propagation part due to a concave lens effect of the light transmission member. Therefore, according to the probe for a photoacoustic measurement apparatus, a wide range of an object to be measured can be irradiated with light.

Further, particularly, when the inner and outer peripheral surfaces of the light transmission member are formed, in shapes that have curvatures, in one common plane in the probe for a photoacoustic measurement apparatus of the invention, the light-emission angle of light emitted from the light transmission member can be increased only in one direction and a light-emission angle can be maintained at a small angle in a direction where an increase of the light-emission angle of light is not desired.

Furthermore, particularly, when the above-mentioned light guide member, the above-mentioned light diffusion member, and the lens having negative power are disposed in the probe for a photoacoustic measurement apparatus of the invention, a light irradiation range on the object to be measured can be further increased due to the operations of these. The reason for this will be described in detail with reference to embodiments to be described below.

Moreover, since the photoacoustic measurement apparatus according to the invention includes the above-mentioned probe for a photoacoustic measurement apparatus according to the invention, the photoacoustic measurement apparatus can irradiate a wide range of an object to be measured, with light.

DESCRIPTION OF THE PREFERRED EMBODIMENTS

Figure 1:
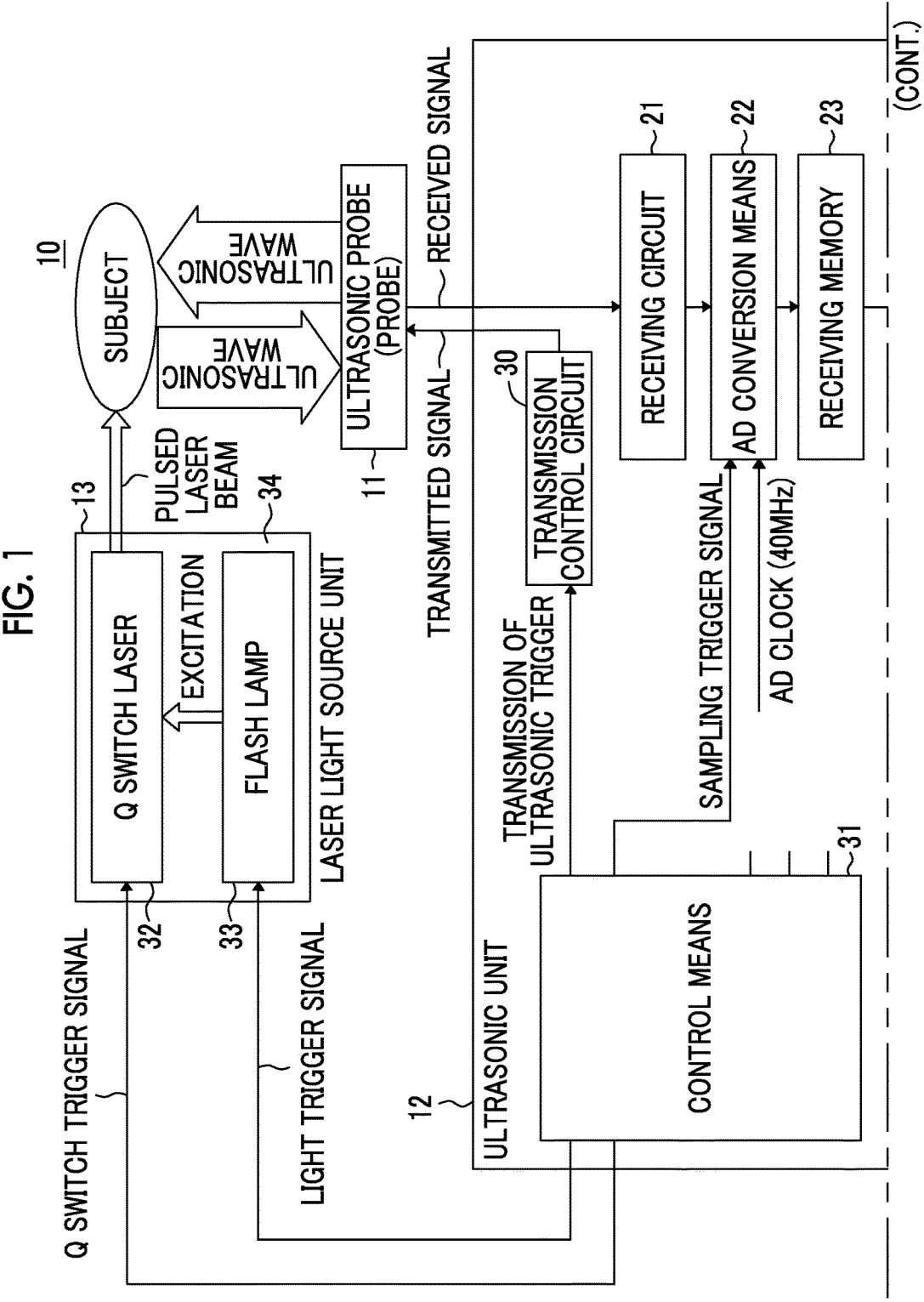
FIG. 1 is a block diagram showing the schematic configuration of an example of a photoacoustic measurement apparatus to which a probe of the invention is applied.

Embodiments of the invention will be described in detail below with reference to the drawings. FIG. 1 is a block diagram showing the basic configuration of a photoacoustic measurement apparatus to which a probe 11 for a photoacoustic measurement apparatus according to an embodiment of the invention is applied. This photoacoustic measurement apparatus is a photoacoustic imaging apparatus 10 as an example, and includes an ultrasonic unit 12, a laser light source unit 13, and image display means 14 in addition to an ultrasonic probe (probe) 11 according to the invention.

Meanwhile, in the following description, an elastic wave generated from the probe 11 is referred to as an ultrasonic wave and an elastic wave generated from a portion of a subject, which is irradiated with light emitted from the probe 11, due to a photo-acoustic effect is referred to as a photoacoustic wave.

The laser light source unit 13 emits a laser beam having a center wavelength of, for example, 800 nm. A pulsed laser beam emitted from the laser light source unit 13 is applied to the subject. It is preferable that this laser beam be guided to the probe 11 by light guide means, such as a plurality of optical fibers, and be applied to the subject from a portion of the probe 11. This laser beam is formed substantially in the shape of a fan beam as described below, and is applied to the subject.

The probe 11 detects an elastic wave (photoacoustic wave) that is generated when an observation object present in the subject absorbs the pulsed laser beam. For this purpose, the probe 11 includes an ultrasonic transducer array including a plurality of ultrasonic transducers that are arranged in parallel in a direction intersecting with a scanning direction caused by, for example, a manual operation to be described below. The probe 11 detects the photoacoustic wave and outputs a photoacoustic wave-detection signal. Meanwhile, the plurality of ultrasonic transducers are disposed so as to be arranged in a line in a plane parallel to the spread plane of a laser beam that is formed substantially in the shape of a fan beam (this will be described below in detail).

When the photoacoustic image of the subject is acquired, the probe 11 is moved in the direction intersecting with the spread plane of the laser beam. Accordingly, the subject is two-dimensionally scanned with a laser beam. This scanning may be performed through the movement of the probe 11 that is performed by a tester's manual operation, or more accurate two-dimensional scanning may be realized using a scanning mechanism.

The ultrasonic unit 12 includes a receiving circuit 21, AD conversion means 22, a receiving memory 23, data separating means 24, image reconstruction means 25, detection/logarithmic conversion means 26, and image construction means 27. The output of the image construction means 27 is input to the image display means 14 that is formed of, for example, a CRT, a liquid crystal display, or the like. Further, the ultrasonic unit 12 includes control means 31 for controlling the operation of a transmission control circuit 30, the operation of each part of the ultrasonic unit 12, and the like.

The receiving circuit 21 receives the photoacoustic wave-detection signal that is output from the probe 11. The AD conversion means 22 is sampling means. The AD conversion means 22 samples the photoacoustic wave-detection signal, which is received by the receiving circuit 21, and converts the photoacoustic wave-detection signal into photoacoustic data that is a digital signal. This sampling is performed at a predetermined sampling cycle in synchronization with, for example, an AD clock signal that is input from the outside.

The laser light source unit 13 includes a Q-switch pulsed laser 32 that is formed of a Ti: Sapphire laser, an alexandrite laser, or the like, and a flash lamp 33 that is an excitation light source of the Q-switch pulsed laser 32. A light trigger signal, which instructs light to be emitted, is input to the laser light source unit 13 from the control means 31. When the laser light source unit 13 receives the light trigger signal, the laser light source unit 13 excites the Q-switch pulsed laser 32 by turning on the flash lamp 33. For example, when the flash lamp 33 sufficiently excites the Q-switch pulsed laser 32, the control means 31 outputs a Q switch trigger signal. When the Q-switch pulsed laser 32 receives the Q switch trigger signal, the Q-switch pulsed laser 32 turns on a Q switch thereof and emits a pulsed laser beam having a wavelength of 800 nm.

Here, the time, which is required until the Q-switch pulsed laser 32 is sufficiently excited after the flash lamp 33 is turned on, can be estimated based on the characteristics of the Q-switch pulsed laser 32. Meanwhile, instead of controlling the Q switch from the control means 31 as described above, it may be possible to turn on the Q switch after the sufficient excitation of the Q-switch pulsed laser 32 occurs in the laser light source unit 13. In this case, a signal indicating that the Q switch is turned on may be sent to the ultrasonic unit 12.

The photoacoustic measurement apparatus of the invention may be configured to acquire an ultrasonic image, which is obtained from a reflected ultrasonic wave, in addition to a photoacoustic image. A case in which the photoacoustic measurement apparatus of the invention is configured in this way will be described below. The control means 31 inputs an ultrasonic trigger signal, which instructs an ultrasonic wave to be transmitted, to the transmission control circuit 30. When the transmission control circuit 30 receives this ultrasonic trigger signal, the transmission control circuit 30 allows an ultrasonic wave to be transmitted from the probe 11. The control means 31 outputs a light trigger signal first, and then outputs an ultrasonic trigger signal. When the light trigger signal is output, the irradiation of a subject with a laser beam and the detection of a photoacoustic wave are performed. Then, an ultrasonic trigger signal is output, so that the transmission of an ultrasonic wave to the subject and the detection of a reflected ultrasonic wave are performed. Here, in order to transmit an ultrasonic wave from the probe 11, the ultrasonic transducer array may also be used as an ultrasonic transducer array for the detection of a photoacoustic wave or an ultrasonic transducer array different from the ultrasonic transducer array may be used.

The control means 31 outputs a sampling trigger signal, which instructs sampling to start, to the AD conversion means 22. This sampling trigger signal is output after the output of the light trigger signal and before the output of the ultrasonic trigger signal, and more preferably, at a timing where a subject is actually irradiated with a laser beam. For this reason, the sampling trigger signal is output in synchronization with, for example, a timing where the control means 31 outputs the Q switch trigger signal. When the AD conversion means 22 receives the sampling trigger signal, the AD conversion means 22 starts the sampling of the photoacoustic wave-detection signal, which is output from the probe 11 and is received by the receiving circuit 21.

After outputting the light trigger signal, the control means 31 outputs the ultrasonic trigger signal at a timing where the detection of a photoacoustic wave has ended. At this time, the AD conversion means 22 continues to perform the sampling of the photoacoustic wave-detection signal without stopping the sampling of the photoacoustic wave-detection signal. In other words, the control means 31 outputs the ultrasonic trigger signal while the AD conversion means 22 continues to perform the sampling of the photoacoustic wave-detection signal. When the probe 11 transmits an ultrasonic wave in response to the ultrasonic trigger signal, an object to be detected by the probe 11 is changed into a reflected ultrasonic wave from a photoacoustic wave. The AD conversion means 22 continuously samples the photoacoustic wave-detection signal and the ultrasonic wave-detection signal by continuing to perform the sampling of the detected ultrasonic wave-detection signal.

The AD conversion means 22 stores photoacoustic data and ultrasonic data, which are obtained through the sampling, in the common receiving memory 23. Sampling data, which is stored in the receiving memory 23, is photoacoustic data until a certain point of time, and is ultrasonic data after the certain point of time. The data separating means 24 separates the photoacoustic data and the ultrasonic data that are stored in the receiving memory 23.

The generation and display of a photoacoustic image or a reflected ultrasonic image will be described below. The ultrasonic data, which is read from the receiving memory 23, and the photoacoustic data, which is obtained when a subject is irradiated with a pulsed laser beam having a wavelength of 800 nm, are input to the data separating means 24 of FIG. 1. The data separating means 24 inputs only photoacoustic data to the image reconstruction means 25, which is provided on the rear stage, when the photoacoustic image is generated. The image reconstruction means 25 reconstructs data, which represents the photoacoustic image, on the basis of the photoacoustic data.

The detection/logarithmic conversion means 26 generates an envelope of the data representing the photoacoustic image, and then widens a dynamic range by logarithmically converting the envelope. The detection/logarithmic conversion means 26 inputs the data, which has been subjected to these kinds of processing, to the image construction means 27. The image construction means 27 constructs a photoacoustic image of a cross-section, which is scanned with a pulsed laser beam, on the basis of the input data, and inputs data representing the photoacoustic image to the image display means 14. Accordingly, the photoacoustic image of the cross-section is displayed on the image display means 14.

Meanwhile, it is also possible to two-dimensionally scan the subject with a laser beam by moving the probe 11 as described above, and to generate and display a photoacoustic image, which three-dimensionally displays a desired portion of the subject, for example, a blood vessel or the like, on the basis of image data of a plurality of cross-sections obtained with the scanning.

Further, it is also possible to generate and display the ultrasonic image of the subject on the basis of the ultrasonic data that is separated by the data separating means 24. The generation and display of the ultrasonic image may be performed by a well-known method in the related art. Since the generation and display of the ultrasonic image are not directly related to the invention, the detailed description thereof is omitted. However, the ultrasonic image and the photoacoustic image can also be superimposed and displayed.

Next, the probe 11 will be described in detail. Meanwhile, the photoacoustic imaging apparatus 10 is formed of a portable imaging apparatus shown in FIG. 2 as one example here, and the probe 11 used in the photoacoustic imaging apparatus 10 will be described. First, the portable imaging apparatus of FIG. 2 will be described. This portable imaging apparatus includes an apparatus body 112 and a cover 113. An operation section 114, which is provided with a plurality of buttons, a trackball, and the like used to input various operational instructions to the portable imaging apparatus, is disposed on the upper surface of the apparatus body 112. A monitor 14 (corresponding to the image display means 14 of FIG. 1), which displays a photoacoustic image, an ultrasonic image, and various operation screens, is provided on the inner surface of the cover 113.

Figure 2:
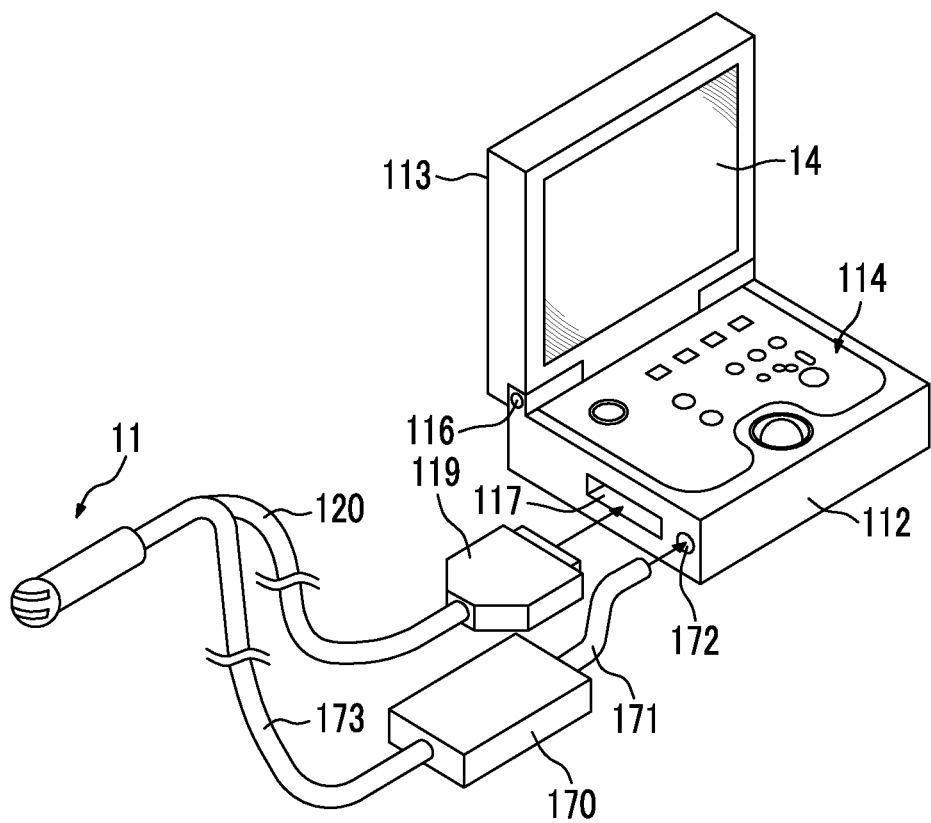
FIG. 2 is a perspective view showing an example of the appearance of the photoacoustic measurement apparatus.

The cover 113 is mounted on the apparatus body 112 through a hinge 116, and is rotatable between an open position, which is shown in FIG. 2 and is a state in which the operation section 114 and the monitor 14 are seen and a closed position (not shown) in which the operation section 114 and the monitor 14 are covered with each other and are protected so that the upper surface of the apparatus body 112 and the inner surface of the cover 113 face each other. Since a grip (not shown) is mounted on one side surface of the apparatus body 112, the portable imaging apparatus can be carried while the apparatus body 112 and the cover 113 are in a closed state. A probe-connection portion 117 to which the probe 11 is detachably connected and a laser unit-connection portion 172 are provided on the other side surface of the apparatus body 112. The probe 11 is electrically connected to the probe-connection portion 117 through a connector 119 and a cable 120.

Meanwhile, for example, a pulsed laser unit 170 in which a Q-switch solid-state laser is built is connected to the laser unit-connection portion 172 through a power cable 171. If light emission is instructed from the operation section 114 of the portable imaging apparatus when a photoacoustic image is acquired, the pulsed laser unit 170 receives a predetermined trigger signal and emits a pulsed laser beam. The pulsed laser beam is propagated through a bundle fiber 173, and is applied to the subject from the probe 11.

Figure 3:
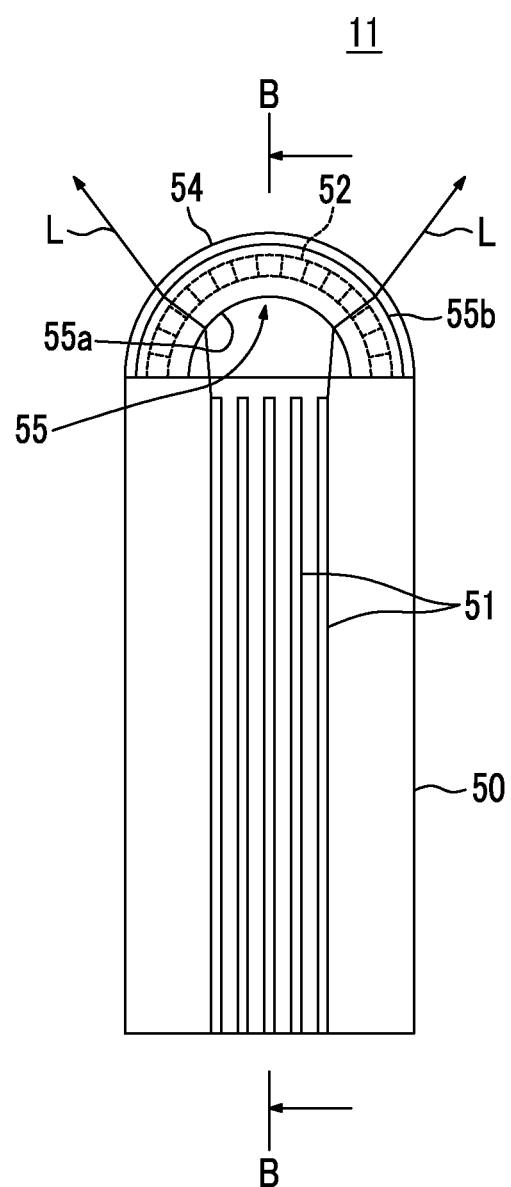
FIG. 3 is a cross-sectional view showing a probe according to a first embodiment of the invention.
Figure 4:
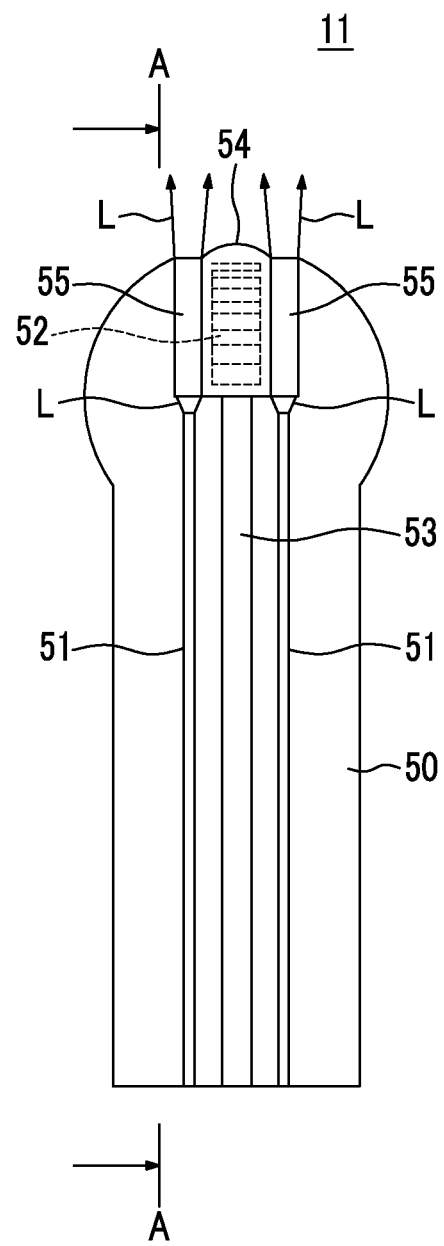
FIG. 4 is a cross-sectional view showing another cross-section of the probe of FIG. 3.

Next, the probe 11 will be described in detail. FIGS. 3 and 4 are cross-sectional views of the probe 11 according to a first embodiment of the invention taken along planes that are different from each other. That is, FIG. 3 shows the cross-sectional shape of the surface taken along line A-A of FIG. 4, and FIG. 4 shows the cross-sectional shape of the surface taken along line B-B of FIG. 3.

The probe 11 of this embodiment is for example, mainly transrectally and transvaginally used while being held by an operator's hand. The probe 11 includes a substantially columnar body 50 made of, for example, a resin or the like. A plurality of optical fibers 51 that serve as a light propagation part, an ultrasonic transducer array 52 that is formed of a plurality of ultrasonic transducers, a substrate/wiring portion 53 that includes a circuit for transmitting ultrasonic waves and receiving photoacoustic waves generated in the subject, and light transmission members 55 are disposed in the body 50. Further, an acoustic lens 54, which converges the ultrasonic waves and the photoacoustic waves, is mounted on the outside of the ultrasonic transducer array 52.

Ten optical fibers 51 are used in this embodiment, and a set of five optical fibers 51 arranged in a row is disposed on each of both surfaces of the substrate/wiring portion 53. The respective base ends (lower ends in FIG. 2) of these optical fibers 51 are optically connected to the bundle fiber 173 shown in FIG. 2, but the connection structure thereof is not shown. Meanwhile, for example, thin light guide plates or the like may be applied as the light propagation part other than the optical fibers 51.

The ultrasonic transducer array 52 serving as a photoacoustic wave detector is an array in which a plurality of ultrasonic transducers are disposed along one arc. That is, the ultrasonic transducer array 52 is formed of an array of which an outer end face is formed in a so-called convex shape. Meanwhile, an inorganic ultrasonic transducer to which an inorganic piezoelectric thin film made of a lead zirconate titanate (Pb(Zr,Ti)O3)-based material, such as PZT (registered trademark), is applied or an organic ultrasonic transducer to which an organic piezoelectric thin film made of fluoride-based material, such as PVDF or P(VDF-TrFE), is applied can be used as the ultrasonic transducer. In addition, the ultrasonic transducer array 52 may be formed by the combination of the inorganic ultrasonic transducers and the organic ultrasonic transducers.

A total of two light transmission members 55 are disposed so that one light transmission member corresponds to one set of five optical fibers 51. Each light transmission member 55 is made of a material having high transmissivity, such as optical glass or a synthetic resin, and is formed in a shape in which a part (a half in this embodiment) of an annular plate is cut. That is, an inner peripheral surface 55a and an outer peripheral surface 55b of the light transmission member 55 are formed in the shapes along two circles that are concentric circles, respectively. Accordingly, the radius of curvature of the outer peripheral surface 55b, which is a convex surface, is larger than the radius of curvature of the inner peripheral surface 55a that is a concave surface. Further, the inner peripheral surface 55a and the outer peripheral surface 55b of the light transmission member 55 are formed, in shapes that have curvatures, in one common plane. Furthermore, each light transmission member 55 is disposed so that the outer peripheral surface 55b extends along the outer end face of the ultrasonic transducer array 52. Meanwhile, the radius of curvature of the inner peripheral surface 55a and the radius of curvature of the outer peripheral surface 55b satisfy a relationship in which the latter is absolutely larger than the former.

Laser beams L, which are emitted from one set of five optical fibers 51, are incident on the light transmission member 55 from the inner peripheral surface 55a, are transmitted through the inside of the light transmission member 55, and are emitted from the outer peripheral surface 55b. In this case, the laser beams L are emitted so as to spread at an angle, which is larger than an emission angle obtained when the laser beams are emitted from one set of five optical fibers 51, in a surface (the surface shown in FIG. 3) parallel to the semi-annular side surface of the light transmission member 55 by a concave lens effect of the light transmission member 55 that is formed in the above-mentioned shape. Meanwhile, since the concave lens effect of the light transmission member 55 is not generated in a surface (the surface shown in FIG. 4) perpendicular to the semi-annular side surface of the light transmission member 55, the laser beams L are emitted so as to hardly spread.

Two laser beams L, which are formed substantially in the shape of a fan beam, are emitted from the probe 11 as described above, and a portion, which is to be imaged, of the subject, is irradiated with these laser beams. When the emission angle of the laser beam L is widened as described above since the scanning direction of the laser beam L relative to the subject is a direction substantially perpendicular to the plane of FIG. 3 (a lateral direction in FIG. 4), a large irradiation angle on the subject is ensured. In this case, it is possible to acquire a photoacoustic image over the wide range of the subject.

Meanwhile, as apparent from the above description, a light transmission unit, which irradiates the subject with light, of the probe 11 of this embodiment, includes the optical fibers 51 and the light transmission members 55.

Here, it is preferable that the acoustic lens 54 and a surface portion of the body 50 in the vicinity of the acoustic lens 54 have optical characteristics, such as an average diffuse reflectance of 85% or more and an average absorptance of 10% or less, in the wavelength region of the laser beam L. When such optical characteristics are given, it is possible to suppress the absorption of the laser beam L, which is reflected from the subject, in the ultrasonic transducer array 52 through the acoustic lens 54 or to suppress the absorption of the laser beam L in the acoustic lens 54. Accordingly, it is possible to suppress the generation of an artifact from being caused by the irradiation with the laser beam L.

Meanwhile, the optical characteristics of the surface portion of the body 50 can be given by paint that contains, for example, a first inorganic pigment. In this case, it is preferable that the first inorganic pigment be particles of at least one kind of oxide among a titanium oxide, a zirconium oxide, an iron oxide, and a cerium oxide. Further, it is preferable that the particle size of the first inorganic pigment be in the range of 0.05 to 0.35 µm and it is preferable that the amount of the first inorganic pigment to be added be in the range of 2 to 65 wt %.

Furthermore, the optical characteristics of the surface portion can also be given by a diffusion-reflection sheet.

On addition, it is possible to give the optical characteristics of the surface portion by forming the surface portion with a highly reflective material. In this case, it is preferable that the highly reflective material be polyester, polyethylene, polycarbonate, polytetrafluoroethylene (PTFE), perfluoroalkoxy fluororesin (PFA), a tetrafluoroethylene-hexafluoropropylene copolymer (FEP), an ethylene-ethylene tetrafluoride copolymer (FEP), or an ethylene-chlorotrifluoroethylene copolymer (ECTFE) containing an inorganic pigment.

On the other hand, it is possible to give the optical characteristics of the acoustic lens 54 by forming the acoustic lens 54 with, for example, a material containing a second inorganic pigment. In this case, it is preferable that the second inorganic pigment be particles of at least one kind of oxide among a titanium oxide, a zirconium oxide, an iron oxide, and a cerium oxide. Further, it is preferable that the particle size of the second inorganic pigment be in the range of 0.05 to 0.35 µm and it is preferable that the amount of the second inorganic pigment to be added be in the range of 2 to 65 wt %.

Furthermore, it is preferable that the surface of the body 50 and/or the acoustic lens 54 be covered with a protective layer.

Figure 5:
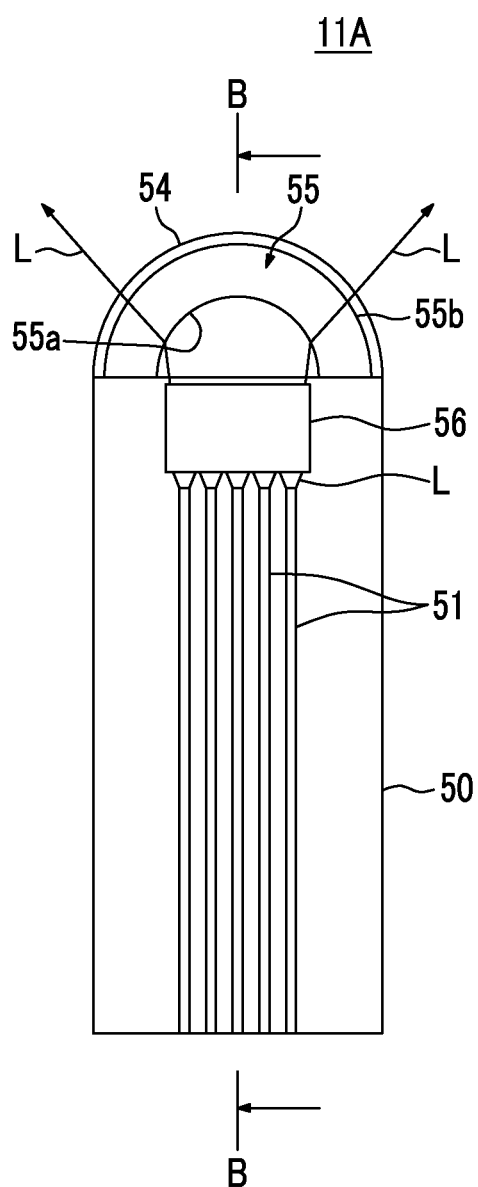
FIG. 5 is a cross-sectional view showing a probe according to a second embodiment of the invention.
Figure 6:
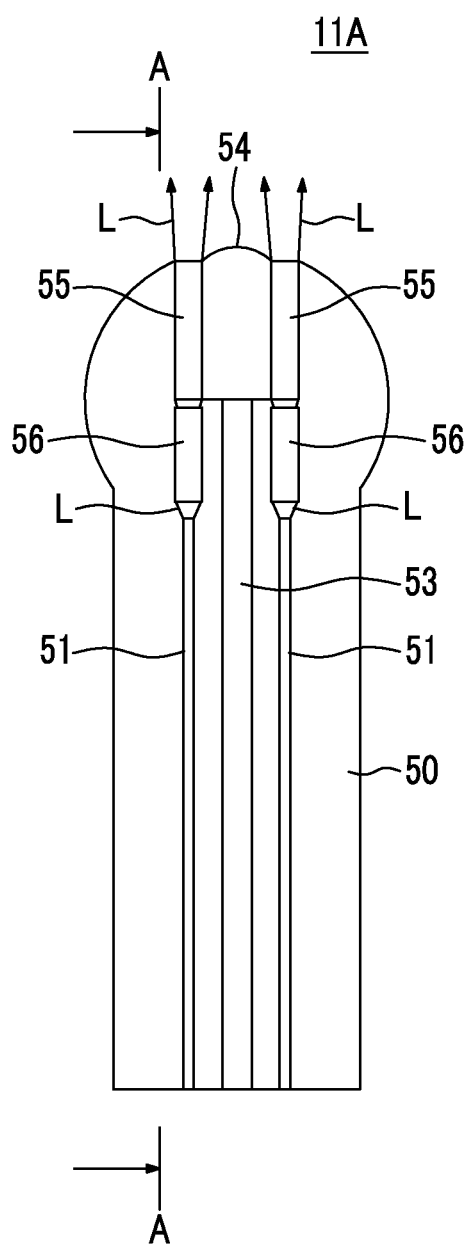
FIG. 6 is a cross-sectional view showing another cross-section of the probe of FIG. 5.

Next, a probe 11A according to a second embodiment of the invention will be described with reference to FIGS. 5 and 6. Meanwhile, the same elements of FIGS. 5 and 6 as the elements of FIGS. 3 and 4 are denoted by the same reference numerals, and the description thereof will be omitted as long as the same elements do not need to be particularly described (The same applies hereinafter). Further, since the positions of the cross-sections shown in FIGS. 5 and 6 are the same as those in FIGS. 3 and 4, the positions of the cross-sections are likewise denoted by "A" and "B" and the repeated description thereof will also be omitted (The same applies hereinafter).

The probe 11A according to the second embodiment is basically different from the probe 11 shown in FIGS. 3 and 4 in that light guide members 56 are disposed between optical fibers 51 and light transmission members 55. The light guide member 56 is a member that is obtained by performing special processing on the surface of, for example, a thin rectangular parallelepiped acrylic plate or quartz plate so that the member uniformly emits light having been incident from one end face thereof (the lower end face in FIGS. 5 and 6) from the other end face thereof (the upper end face in FIGS. 5 and 6). It is possible to produce the light guide member 56 by forming a thin resin film, which has low refractive index, on the side surfaces of, for example, a quartz plate. In the case of this structure, a laser beam L, which is incident from the lower end face of the light guide member 56, is totally reflected at an interface between the quartz plate and the thin resin film, is propagated during the repetition of the multiple reflection, and is emitted from the upper end face of the light guide member 56.

Since the distribution of the intensity of the laser beam L, which is emitted from the light guide member 56 and is incident on the light transmission member 55, is uniformized by the above-mentioned repetition of the multiple reflection of the laser beam L, it is possible to irradiate each portion of the subject with light having more uniform intensity. Further, since the light transmission members 55 are also provided in this embodiment, the same effects as the effects of the first embodiment can be obtained with the light transmission members 55. The above-mentioned effects are also likewise obtained from third to seventh embodiments to be described below.

Next, a probe 11B according to a third embodiment of the invention will be described with reference to FIGS. 7 and 8. The probe 11B according to the third embodiment is basically different from the probe 11A shown in FIGS. 5 and 6 in that light diffusion members 57 are disposed between optical fibers 51 and light guide members 56. The light diffusion member 57 is generally referred to as a homogenizer, and has a function of diffusing a laser beam L incident from the optical fiber 51 and a function of making the top of the energy profile (energy distribution) of the laser beam L flat.

On other words, "making the top of the energy profile flat" as described above means to form the laser beam L, which is incident on the light diffusion member 57, into a laser beam of which the central portion has a flat-top energy profile. "Flat-top" means a state in which, when a concentric circle in which the diameter of the energy profile of the laser beam L emitted from the light diffusion member 57 is 80% of the beam diameter is taken and a standard deviation of the energy of each point in this concentric circle is obtained, the standard deviation is within 25% of the average energy in this concentric circle. In general, the structure of the light diffusion member 57 is designed so that light is made completely flat-top at infinity, that is, the standard deviation is substantially equal to 0.

However, an energy profile, when the laser beam L is incident on the light guide member 56, does not necessarily need to be in a complete flat-top state, and is sufficient to be in a flat-top state substantially within the above-mentioned range.

Since the top of the energy profile of the laser beam L is made flat as described above, the variation of the intensity of the laser beam L, which is applied to the subject, at certain portions of the subject is prevented.

Further, since the light diffusion member 57 diffuses the incident laser beam L, the laser beam L, which is emitted from the light guide member 56 and is incident on the light transmission member 55, is incident in a wider angular range. Accordingly, it is possible to irradiate the wider range of the subject with a laser beam L in this embodiment than a case in which the probe 11A according to the second embodiment is used.

Effects, which are obtained through the above-mentioned light diffusion member 57, are also likewise obtained from fourth to seventh embodiments to be described below.

Meanwhile, the light diffusion member 57 may be formed of a single optical element, and may be formed by the combination of a plurality of optical elements. It is preferable that a lens diffuser in which small lens-like portions are randomly disposed on one surface of a substrate be used as a single optical element. For example, an engineered diffuser manufactured by RPC Photonics, Inc. can be used as the lens diffuser. It is possible to substantially arbitrarily change the energy profile and the shape of the laser beam L by using this element. Meanwhile, preferred examples of the light diffusion member 57, which is formed of such an element, include a light diffusion member of which (an emission angle in the plane shown in FIG. 7)×(an emission angle in the plane shown in FIG. 8) is 60°×10° and a light diffusion member of which (an emission angle in the plane shown in FIG. 7)×(an emission angle in the plane shown in FIG. 8) is 89°×25°.

Figure 7:
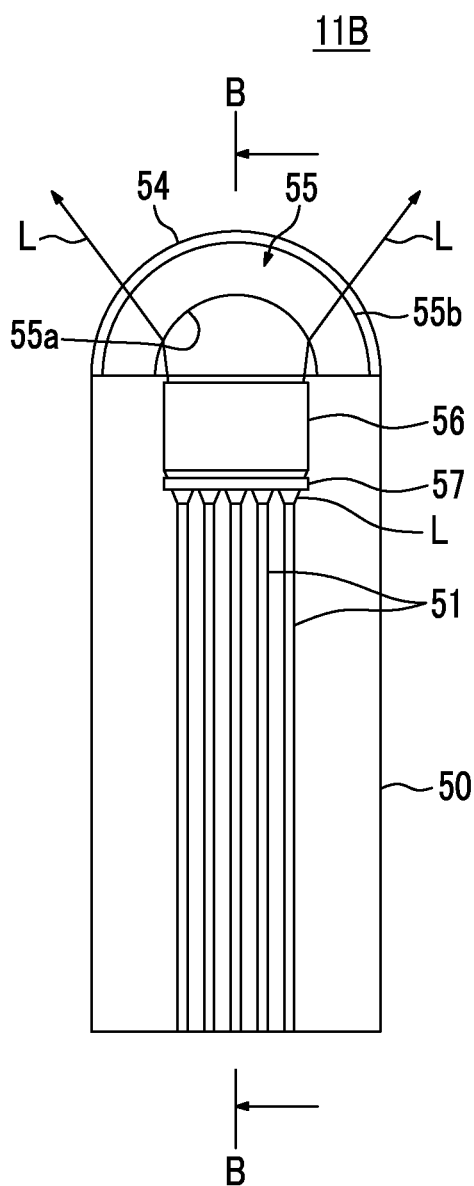
FIG. 7 is a cross-sectional view showing a probe according to a third embodiment of the invention.
Figure 8:
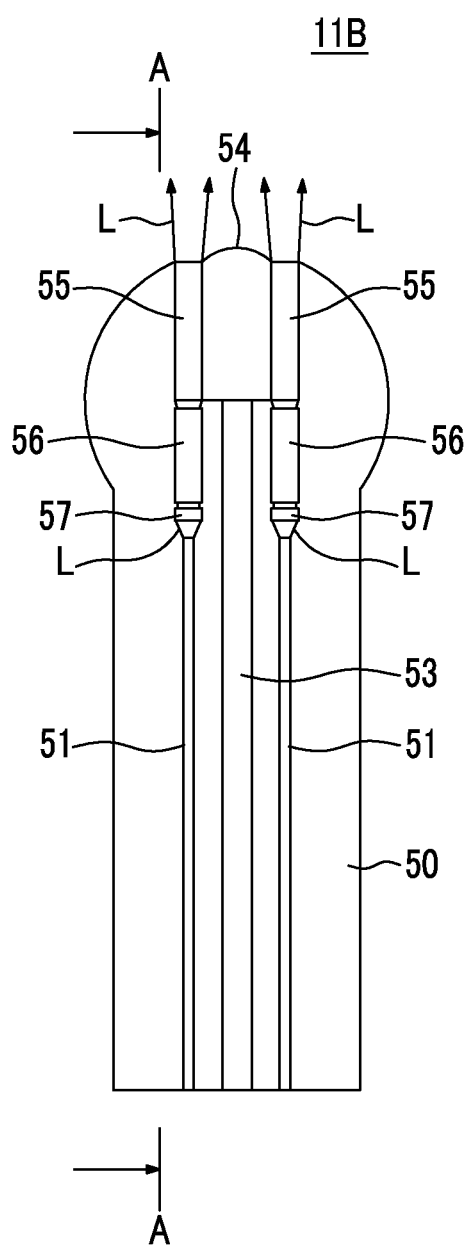
FIG. 8 is a cross-sectional view showing another cross-section of the probe of FIG. 7.
Figure 18:
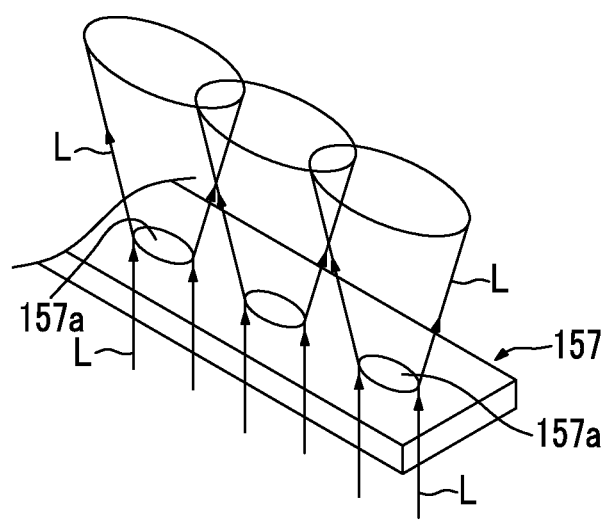
FIG. 18 is a perspective view showing an example of a light diffusion member that is applied to the probe of the invention.

On particular, since there is a demand for the improvement of light-use efficiency through the prevention of the spread of laser beams L in the plane shown in FIG. 8 in the probe 11B of this embodiment, it is preferable to apply an anisotropic light diffusion member of which a light diffusion effect in the plane shown in FIG. 7 is significantly larger than that in the plane shown in FIG. 8. Examples of such a light diffusion member include a so-called elliptical diffuser 157 in which elliptical diffusion elements 157a diffusing a laser beam L in an elliptical shape are disposed so as to be aligned in the direction of a major axis of the elliptical diffusion element as shown in FIG. 18.

When the light diffusion member 57 is formed of a single optical element as described above, it is possible to further simplify the structure of a light-transmission optical system.

Next, a probe 11C according to a fourth embodiment of the invention will be described with reference to FIG. 9. The probe 11C according to the fourth embodiment is basically different from the probe 11B shown in FIGS. 7 and 8 in terms of the size of a light guide member 56 and the size of a light diffusion member 57. That is, the size of the light guide member 56 of this embodiment is set so that a part of a light-emitting end face (the upper end face in FIG. 9) of the light guide member 56 faces a lower end face 55c of the light transmission member 55. Meanwhile, the lower end face 55c of the light transmission member 55 is a flat end face that connects the inner peripheral surface 55a to the outer peripheral surface 55b.

According to the above-mentioned structure, in the probe 11C of this embodiment, a light component, which goes straight into the light transmission member 55 from the light guide member 56 through the lower end face 55c, is superimposed on the laser beam L emitted from the light transmission member 55. Accordingly, in this case, a subject can be irradiated with a laser beam L of which the intensity is further uniformized.

Next, a probe 11D according to a fifth embodiment of the invention will be described with reference to FIG. 10. The probe 11D according to the fifth embodiment is basically different from the probe 11B shown in FIGS. 7 and 8 in terms of the shape of a light guide member 56A. That is, the light guide member 56A of this embodiment is formed in a tapered shape so that the width of a portion of the light guide member 56A close to the light transmission member 55 is larger than the width of a portion of the light guide member 56A close to the optical fiber 51 and the cross-sectional area of the light guide member 56A is gradually increased toward the light transmission member 55 from the optical fiber 51.

According to the above-mentioned structure, in the probe 11D of this embodiment, light components, which are incident on left and right side end faces of the light guide member 56A at a small incident angle, are reduced in comparison with a case in which the thin rectangular parallelepiped light guide member 56 shown in FIG. 7 is used. Light components, which are incident on the left and right side end faces of the light guide member 56 at a smaller incident angle, often pass through the side end faces without being totally reflected by the left and right side end faces. Accordingly, when the light components, which are incident on the left and right side end faces of the light guide member 56A at a small incident angle, are reduced as described above, the leakage of the laser beam L from the light guide member 56A can be suppressed and light-use efficiency can be improved.

Next, a probe 11E according to a sixth embodiment of the invention will be described with reference to FIG. 11. The probe 11E according to the sixth embodiment is basically different from the probe 11D shown in FIG. 10 in terms of the size of a light guide member 56B and the size of a light diffusion member 57. That is, the width of the upper end face of the tapered light guide member 56B of this embodiment is larger than that of the light guide member 56A of FIG. 10. Accordingly, a part of the upper end face (light-emitting end face) of the light guide member 56B faces the lower end face 55c of the light transmission member 55.

Figure 9:
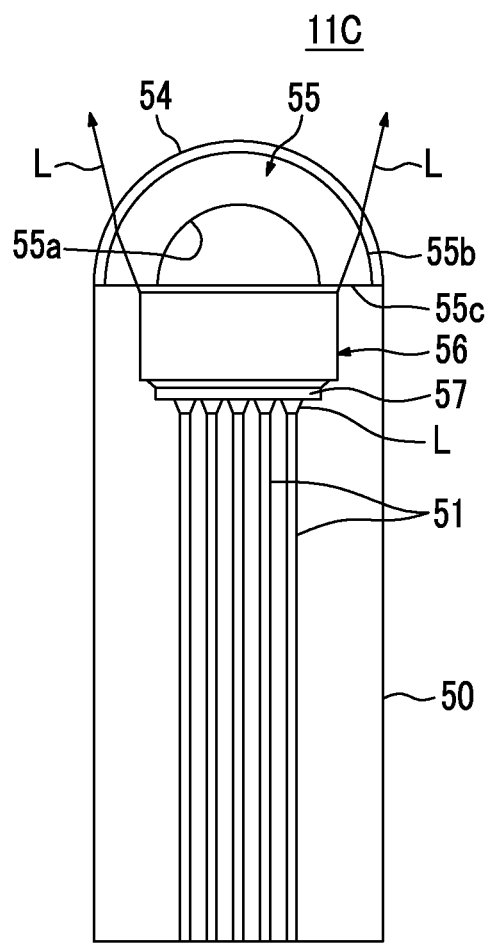
FIG. 9 is a cross-sectional view showing a probe according to a fourth embodiment of the invention.

According to the above-mentioned structure, even in the probe 11E of this embodiment, a light component, which goes straight into the light transmission member 55 from the light guide member 56B through the lower end face 55c, is superimposed on the laser beam L emitted from the light transmission member 55 as in the probe 11C shown in FIG. 9. Accordingly, even in this case, a subject can be irradiated with a laser beam L of which the intensity is further uniformized.

Figure 11:
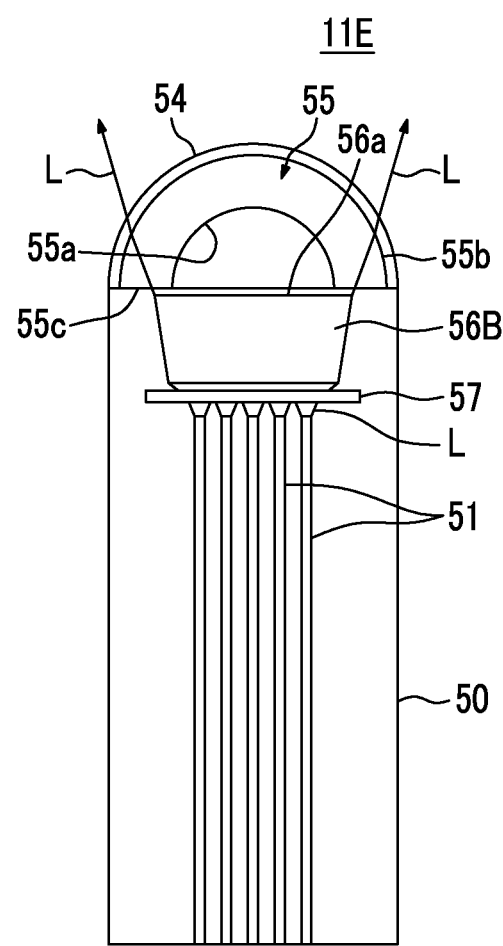
FIG. 11 is a cross-sectional view showing a probe according to a sixth embodiment of the invention.
Figure 12:
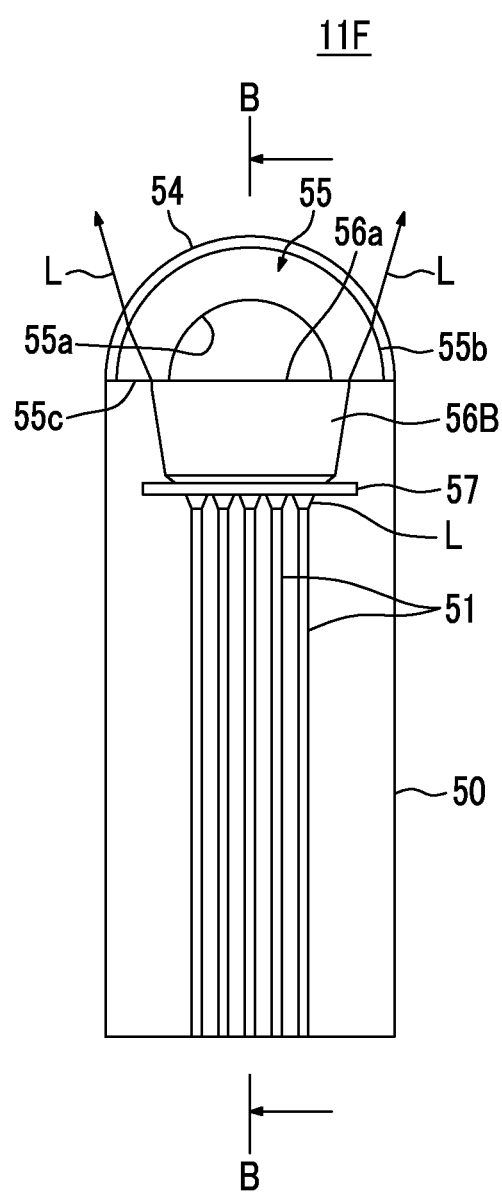
FIG. 12 is a cross-sectional view showing a probe according to a seventh embodiment of the invention.
Figure 13:
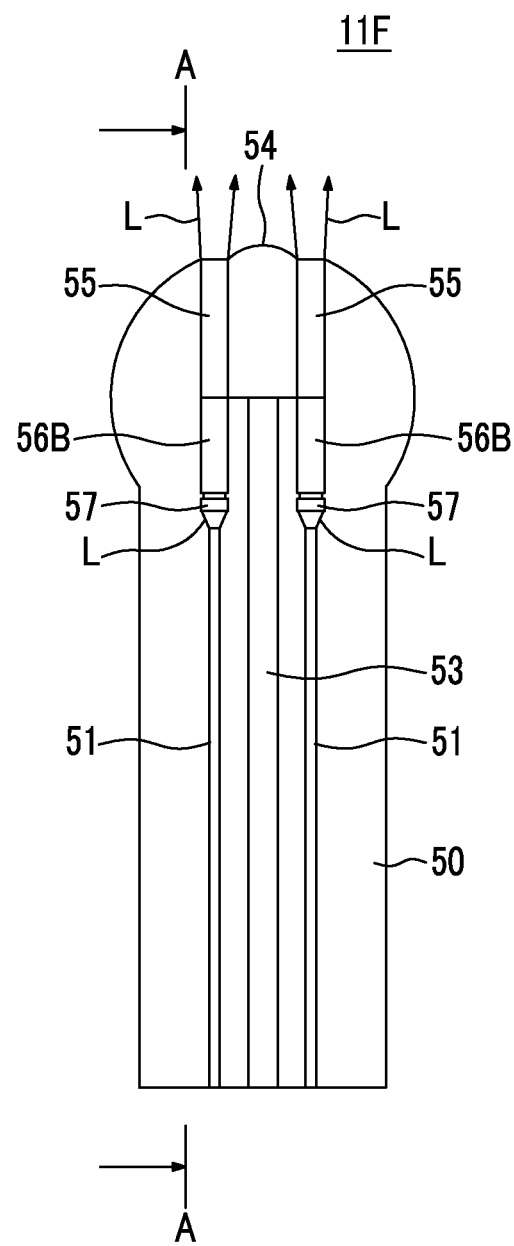
FIG. 13 is a cross-sectional view showing another cross-section of the probe of FIG. 12.

Next, a probe 11F according to a seventh embodiment of the invention will be described with reference to FIGS. 12 and 13. The probe 11F according to the seventh embodiment is basically different from the probe 11E shown in FIG. 11 in terms of the disposition of light guide members 56B. That is, a part of the upper end face (light-emitting end face) of the light guide member 56B of this embodiment comes into close contact with the lower end face 55c of the light transmission member 55.

Accordingly, even in this case, an effect of irradiating a subject with a laser beam L of which the intensity is further uniformized is obtained and work for adjusting the position between the light transmission member 55 and the light guide member 56B is also easily performed as in the sixth embodiment. Further, in the case of this structure, the light transmission members 55 and the light guide members 56B can also be integrally molded with a resin or the like. Accordingly, work for assembling the probe 11F is simplified in this case.

Next, a probe 11G according to an eighth embodiment of the invention will be described with reference to FIG. 19. The probe 11G according to the eighth embodiment is basically different from the probe 11A shown in FIG. 5 in that three concave lenses 71, 72, and 73 are provided between light guide members 56 and light transmission members 55. Meanwhile, these concave lenses 71, 72, and 73 have a constant shape in a direction perpendicular to the plane of FIG. 19 so as to correspond to the flat light transmission members 55 (see FIG. 6 and the like). It is possible to produce such a concave lens by cutting, for example, a cylindrical lens to a small thickness in a plane that is orthogonal to the axis of the cylindrical lens.

In the above-mentioned structure, an operation for diffusing a laser beam L is obtained by the three concave lenses 71, 72, and 73 having negative power. Accordingly, a laser beam L is incident on the light transmission member 55 at a wide angular range in comparison with a case in which the concave lenses 71, 72, and 73 are not provided. Therefore, the emission angle of the laser beam L, which is emitted from the light transmission member 55, is also further increased.

Figure 10:
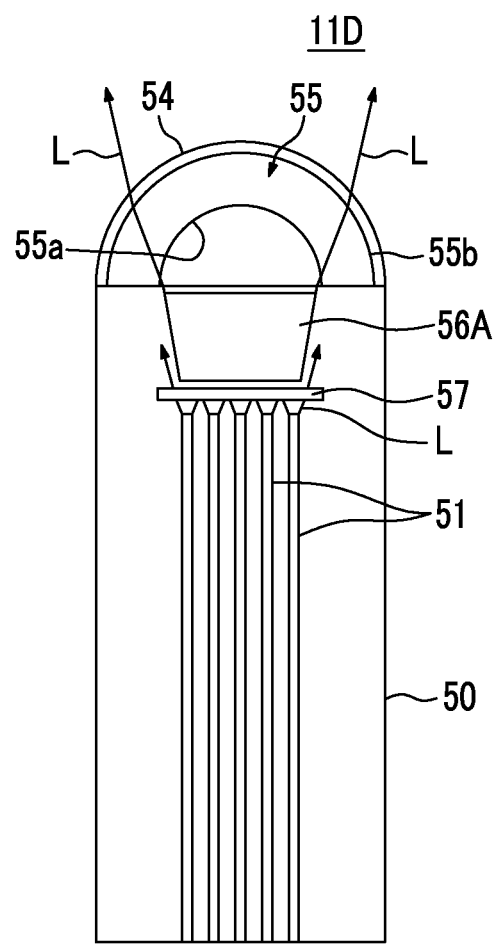
FIG. 10 is a cross-sectional view showing a probe according to a fifth embodiment of the invention.

When a tapered light guide member like the light guide member 56A shown in FIG. 10 is used as described above, an effect of further increasing the angular range of the laser beam L emitted from the light transmission member 55 is obtained and is the same as the effect obtained from the concave lenses 71, 72, and 73. However, when this kind of concave lens is used, it is possible to reduce the disposition area of the optical member in comparison with a case in which a tapered light guide member is used. Accordingly, it is advantageous to use this kind of concave lens to reduce the size and thickness of the probe.

Figure 19:
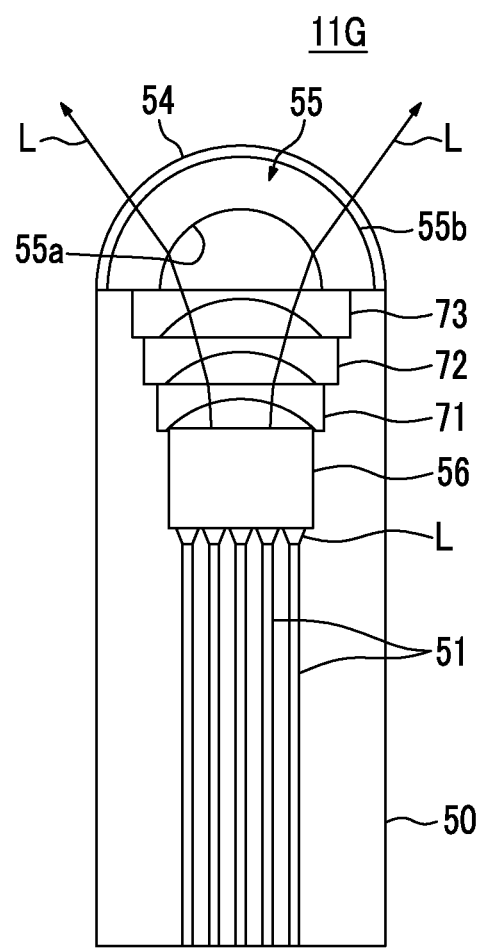
FIG. 19 is a cross-sectional view showing a probe according to an eighth embodiment of the invention.

Meanwhile, all of the concave lenses 71, 72, and 73 applied to this embodiment are plano-concave lenses in the plane shown in FIG. 19, and the radii of curvature of these concave lenses 71, 72, and 73 are −6.6 mm, −7.1 mm, and −9.8 mm as an example, respectively. Further, the lens, which has negative power, used in the invention is not limited to the plano-concave lens. For example, a biconcave lens, a negative meniscus lens, or the like can also be applied as the lens having negative power in addition to the plano-concave lens. Furthermore, the number of the lenses having negative power is also not limited to three as in the embodiment, and lenses of which the number is an appropriate number equal to or larger than one can be applied. Moreover, the concave lenses 71, 72, and 73 have been disposed between the inner peripheral surfaces 55a of the light transmission members 55 and the light guide members 56 in this embodiment, but the light guide members 56 also may be omitted naturally.

Figure 14:
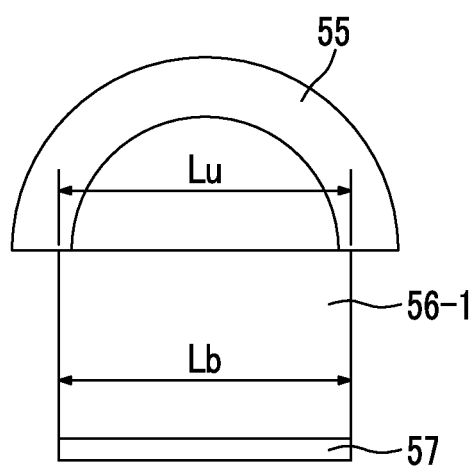
FIG. 14 is a view illustrating the effect of a light guide member that is applied to the probe of the invention.
Figure 15:
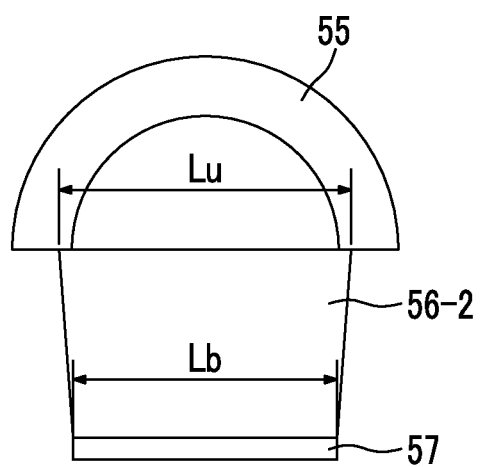
FIG. 15 is a view illustrating the effect of the light guide member that is applied to the probe of the invention.
Figure 16:
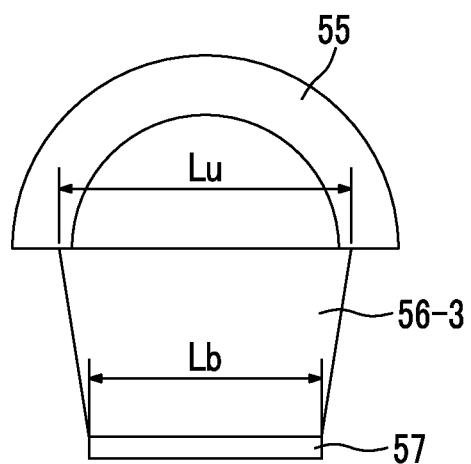
FIG. 16 is a view illustrating the effect of the light guide member that is applied to the probe of the invention.
Figure 17:
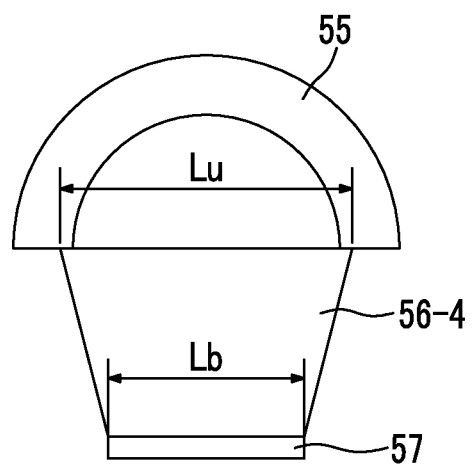
FIG. 17 is a view illustrating the effect of the light guide member that is applied to the probe of the invention.

Here, analysis results of an effect of improving light-use efficiency, which are obtained when tapered light guide members are used, will be described. Here, when four light guide members 56-1, 56-2, 56-3, and 56-4 shown in FIGS. 14 to 17 are used, light-use efficiency is calculated by simulations that are performed by a calculator. A part of the light-emitting end face of each of the four light guide members comes into close contact with the lower end face of the light transmission member 55 as in the seventh embodiment, and the thicknesses of the light guide members are all 3 mm and the widths Lu of the light-emitting end faces thereof are all 16 mm. Further, the light guide member 56-1 of FIG. 14 is a thin rectangular parallelepiped light guide member of which the width Lu of a light-emitting end face and the width Lb of a light incident end face are equal to each other. Meanwhile, the respective light guide members 56-2, 56-3, and 56-4 of FIGS. 15, 16, and 17 are tapered light guide members of which the widths Lb of the light incident end faces are 14 mm, 12 mm, and 11 mm, respectively.

Light-use efficiencies, which are obtained when the four light guide members 56-1, 56-2, 56-3, and 56-4 are used, respectively, are 84%, 87%, 89%, and 90%. Accordingly, it is found that higher light-use efficiency is obtained as the tapered angle becomes larger. Meanwhile, the light-use efficiency, which is obtained here, is a value that is standardized using the energy of light incident on the light diffusion member.

Further, the results of the simulations, which are performed by a calculator, of an aspect in which the angular range (viewing angle) and the light-use efficiency of light emitted from the light transmission member 55 are changed in accordance with the length (a distance between the light incident end face and the light emitting end face) of the tapered (trapezoidal) light guide member as described above, will be shown below.

Here, basically, the structure shown in FIG. 10, that is, a structure in which the tapered light guide members 56A and the light diffusion members 57 are sequentially disposed toward a light source from the light transmission members 55 is examined. Furthermore, the radius of the inner peripheral surface of the light transmission member 55 is 7 mm, the radius of the outer peripheral surface of the light transmission member 55 is 10 mm, the width Lu of the light-emitting end face of the light guide member 56A is 14 mm which is equal to the distance between both ends of the inner peripheral surface of the light transmission member 55, the width Lb of the light incident end face of the light guide member 56A is 6 mm, and the light source width (the length of light incident on the light diffusion member 57 in the lateral direction in FIG. 10) is 5 mm. Moreover, a light diffusion member of which (an emission angle in the plane shown in FIG. 10)×(an emission angle in the plane orthogonal to the plane shown in FIG. 10) is 60°×10° and a light diffusion member of which (an emission angle in the plane shown in FIG. 10)×(an emission angle in the plane orthogonal to the plane shown in FIG. 10) is 89°×25° are considered as the light diffusion member 57. The results obtained when the former is used are shown in Table 1, and the results obtained when the latter is used are shown in Table 2.

TABLE 1

| Light diffusion member: 60° × 10° | | | | | |
|---|---|---|---|---|---|
| Length of light guide member | 0 mm | 5 mm | 10 mm | 15 mm | 20 mm |
| Viewing angle (full angle at half maximum) | 100° | 145° | 160° | 140° | 130° |
| Light-use efficiency | 74.6% | 72.8% | 81.0% | 81.0% | 81.1% |

TABLE 2

| Light diffusion member: 89° × 25° | | | | | |
|---|---|---|---|---|---|
| Length of light guide member | 0 mm | 5 mm | 10 mm | 15 mm | 20 mm |
| Viewing angle (full angle at half maximum) | 130° | 170° | 170° | 160° | 145° |
| Light-use efficiency | 49.6% | 54.3% | 64.8% | 62.3% | 60.6% |

As shown in Tables 1 and 2, light-use efficiency becomes lower as the length of the light guide member becomes shorter. It is considered that the reason for this is that the amount of light reflected and returning from the light-emitting end face of the light guide member is large when the length of the light guide member is short. Further, from the comparison between the results of Table 1 and the results of Table 2, it is understood that the angular range (viewing angle) of light finally emitted from the light transmission member increases but light-use efficiency decreases as the emission angle of light emitted from the light diffusion member becomes larger.

Furthermore, the results of the simulations, which are performed by a calculator, of an aspect in which the viewing angle and light-use efficiency are changed in accordance with the shape of the light transmission member are shown in Table 3. Here, a case in which the above-mentioned light guide member is not used and the light diffusion member is disposed close to the light transmission member is examined. A light diffusion member of which an emission angle× an emission angle is 60°×10° is considered as the light diffusion member, and light source width is 13 mm. Moreover, six examples of which the radii of the outer peripheral surfaces of the light transmission members are all 10 mm and the radii of the inner peripheral surfaces and distances between the centers of the inner and outer peripheral surfaces are different from one another are considered. Here, the distance between the centers is 0 mm when the inner peripheral surface and the outer peripheral surface are positioned on concentric circles (an example of the right-most column in Table 3), and means a distance where the center of the inner peripheral surface is distant from the center of the outer peripheral surface toward the light source. Further, since the radius of the outer peripheral surface is smaller than the radius of the inner peripheral surface in the examples of the three columns from the left in Table 3, these examples are not included in the invention.

TABLE 3

| Radius of inner peripheral surface | +∞ | 17.5 mm | 10.6 mm | 8.1 mm | 7.3 mm | 7 mm |
|---|---|---|---|---|---|---|
| Radius of outer peripheral surface | 10 mm | 10 mm | 10 mm | 10 mm | 10 mm | 10 mm |
| Distance between centers | +∞ | 16 mm | 8 mm | 4 mm | 2 mm | 0 mm |
| Viewing angle (full angle at half maximum) | 95° | 110° | 125° | 140° | 145° | 140° |
| Light-use efficiency | 94.8° | 82.0° | 82.1° | 82.9° | 83.2° | 83.8° |

A viewing angle, which is obtained when only the light diffusion member is used, is separately obtained, but the viewing angle in that case is 105°. Accordingly, as shown in Table 3, it is apparent that an effect of increasing the viewing angle is obtained when a light transmission member is provided.

The preferred embodiments of the invention have been described above. However, the probe for the photoacoustic measurement apparatus of the invention is not limited to the above-mentioned embodiments, and various corrections and modifications of the structures of the above-mentioned embodiments are also included in the scope of the invention.

For example, the above-mentioned photoacoustic imaging apparatus has been configured to also acquire and display an ultrasonic image that is obtained from a reflected ultrasonic wave. However, the probe of the invention may be applied to a photoacoustic imaging apparatus that does not have such a function, and can also be applied to a photoacoustic measurement apparatus other than the photoacoustic imaging apparatus.

What is claimed is:

1. A probe for a photoacoustic measurement apparatus that irradiates a subject with light comprising:
   a photoacoustic wave detector that detects a photoacoustic wave generated from a portion of the subject irradiated with light, the photoacoustic wave detector having a convex outer surface,
   an acoustic lens mounted on the outer surface of the photoacoustic wave detector,
   a body,
   a plurality of optical fibers that propagate light emitted from a light source, the distal tip of each of the plurality of optical fibers being fixed inside the body, and
   a plurality of light transmission members, each of the plurality of light transmission members having an inner peripheral surface formed in the shape of a curved concave surface and an outer peripheral surface having a radius of curvature larger than the radius of curvature of the inner peripheral surface such that the light emitted from the optical fiber is incident on the inner peripheral surface, wherein the plurality of the light transmission members are of a plate shape and the photoacoustic wave detector is disposed between the plurality of light transmission members such that the outer peripheral face of the light transmission members curves along the convex outer surface of the photoacoustic detector.

2. The probe for a photoacoustic measurement apparatus according to claim 1, further comprising:
a quartz plate which is disposed between the inner peripheral surface of the light transmission member and the optical fiber; and
a thin resin film that is formed on the side surfaces of the quartz plate,
wherein the quartz plate and the thin resin film uniformize the distribution of the intensity of light emitted from the optical fiber.

3. The probe for a photoacoustic measurement apparatus according to claim 1, further comprising:
a quartz plate which uniformizes the distribution of the intensity of light emitted from the optical fiber, is disposed between the inner peripheral surface of the light transmission member and the optical fiber.

4. The probe for a photoacoustic measurement apparatus according to claim 1, further comprising:
a quartz plate which uniformizes the distribution of the intensity of light emitted from the optical fiber, is disposed between the inner peripheral surface of the light transmission member and the optical fiber.

5. The probe for a photoacoustic measurement apparatus according to claim 1, further comprising:
a quartz plate which uniformizes the distribution of the intensity of light emitted from the optical fiber, is disposed between the inner peripheral surface of the light transmission member and the optical fiber.

6. The probe for a photoacoustic measurement apparatus according to claim 2,
wherein at least a part of the quartz plate faces at least a part of an end face of the light transmission member that connects the inner and outer peripheral surfaces of the light transmission member.

7. The probe for a photoacoustic measurement apparatus according to claim 2,
wherein the quartz plate is formed in a tapered shape so that the cross-sectional area of the quartz plate is gradually increased from the optical fiber toward the light transmission member.

8. The probe for a photoacoustic measurement apparatus according to claim 6,
wherein the quartz plate is formed in a tapered shape so that the cross-sectional area of the quartz plate is gradually increased from the optical fiber toward the light transmission member.

9. The probe for a photoacoustic measurement apparatus according to claim 2, further comprising:
a light diffusion member is disposed between the quartz plate and the optical fiber.

10. The probe for a photoacoustic measurement apparatus according to claim 6, further comprising:
a light diffusion member is disposed between the quartz plate and the optical fiber.

11. The probe for a photoacoustic measurement apparatus according to claim 7, further comprising:
a light diffusion member is disposed between the quartz plate and the optical fiber.

12. The probe for a photoacoustic measurement apparatus according to claim 9,
wherein the light diffusion member of which the degree of light diffusion in one direction is lower than the degree of light diffusion in a direction orthogonal to the one direction is used as the light diffusion member.

13. The probe for a photoacoustic measurement apparatus according to claim 12,
wherein a light diffusion pattern of the light diffusion member is an elliptical shape.

14. The probe for a photoacoustic measurement apparatus according to claim 1, further comprising:
a lens having negative power is disposed at a position that faces the inner peripheral surface of the light transmission member.

15. The probe for a photoacoustic measurement apparatus according to claim 2, further comprising:
a lens having negative power is disposed at a position facing the inner peripheral surface of the light transmission member between the inner peripheral surface of the light transmission member and the quartz plate.

16. A photoacoustic measurement apparatus comprising:
the probe for a photoacoustic measurement apparatus according to claim 1.

17. The probe for a photoacoustic measurement apparatus according to claim 1, wherein the light transmission member is made of optical glass.

18. The probe for a photoacoustic measurement apparatus according to claim 1, wherein the light transmission member refracts light.

* * * * *